United States Patent [19]

Wong

[11] Patent Number: 5,271,815
[45] Date of Patent: Dec. 21, 1993

[54] METHOD FOR MEASURING GLUCOSE

[75] Inventor: David K. Wong, Del Mar, Calif.

[73] Assignee: VIA Medical Corporation, San Diego, Calif.

[21] Appl. No.: 814,099

[22] Filed: Dec. 26, 1991

[51] Int. Cl.$^5$ .................................... G01N 27/327
[52] U.S. Cl. ......................... 204/153.12; 204/153.1;
204/153.17; 204/400; 204/402; 204/403;
204/415
[58] Field of Search ........... 204/153.1, 153.12, 153.17,
204/402, 403, 415, 400

[56] References Cited

U.S. PATENT DOCUMENTS

| | | | |
|---|---|---|---|
| 3,539,455 | 11/1970 | Clark | 204/1 |
| 3,979,274 | 9/1976 | Newman | 204/415 |
| 4,573,968 | 3/1986 | Parker | 604/67 |
| 4,650,547 | 3/1987 | Gough | 204/1 |
| 4,757,022 | 7/1988 | Shults et al. | 435/291 |
| 4,759,828 | 7/1988 | Young et al. | 204/1 T |
| 4,890,620 | 1/1990 | Gough | 128/635 |
| 4,891,104 | 1/1990 | Liston et al. | 204/153.17 |

*Primary Examiner*—T. Tung

[57] ABSTRACT

This invention provides an electrochemical sensor capable of measuring the glucose level of body fluids, especially blood. More particularly, this invention also relates to the use of such a glucose sensor in an automated bedside blood chemistry system which facilitates the operation of the sensor.

21 Claims, No Drawings

METHOD FOR MEASURING GLUCOSE

BACKGROUND OF THE INVENTION

1. Field of the Invention

This invention relates generally to the diagnostic testing of a body fluid, especially blood, and more particularly, to disposable sensor assemblies for use in automated bedside monitors to measure the glucose content of body fluid.

2. Description of the Related Art

Presently employed electrochemical glucose sensors are essentially modified polarographic oxygen electrode assemblies. They are two or three-electrode electrochemical cells covered by surface layers of an immobilized enzyme, e.g. glucose oxidase. The glucose oxidase layer, for example, not only serves as an electrolyte but also catalyzes the reaction of glucose with oxygen to form gluconic acid and hydrogen peroxide, $H_2O_2$.

$$\text{glucose} + O_2 \rightarrow \text{gluconic acid} + H_2O_2$$

Thus, the glucose level can be quantitatively determined by either measuring the reduction in the oxygen partial pressure, $pO_2$, or increase in $H_2O_2$ by means of the underlying polarographic oxygen electrode assembly. When the glucose sensor operates in the oxygen mode, the working electrode is negatively polarized against a counter electrode to measure the limiting oxygen reduction current, which is proportional to the $pO_2$. Without the enzyme coating, the sensor is a polarographic oxygen electrode. Conversely, the polarity of the applied bias may be reversed and set at another level to measure the anodic current produced by the oxidation of hydrogen peroxide. There are advantages and disadvantages in either mode. If one chooses to use $pO_2$ as an indirect measurement of glucose, then the oxygen partial pressure of the sample must be determined. If hydrogen peroxide is measured, it is no longer necessary to know the $pO_2$ of the sample. However, other compounds in the sample, such as ascorbic acid, may also be oxidized at the same potential as the hydrogen peroxide, $H_2O_2$. These other components can thus produce an interference effect, and render the determination of glucose inaccurate.

In either mode of operation, the glucose sensor must deal with a common problem; that is, in undiluted whole blood, there is a very large excess of glucose relative to oxygen and the reaction of glucose with oxygen becomes oxygen limited. In this case, the sensor is saturated and sensor saturation thus means that the glucose sensor output approaches zero because there is no more oxygen available on the sensor surface, and that the sensor is therefore glucose saturated. In other words, the range of glucose concentrations detectable by such a sensor is very narrow, typically only up to 40 milligrams per deciliter (mg/dl) of blood before reaching saturation. Clinically, a linear response up to 500 mg/dl is required.

Several approaches have been used to expand the useful range of such glucose sensors. For example, in a commercial glucose analyzer manufactured by Yellow Spring Instrument Inc., as disclosed in U.S. Pat. No. 3,539,455 issued to Leland Clark, whole blood samples are diluted prior to each measurement. Yet another approach is to design the sensor in such a way that oxygen is readily available to the enzyme layer across a hydrophobic structure while the access of glucose to the enzyme layer is restricted through a long and narrow hydrophillic path such as those schemes described in U.S. Pat. Nos. 4,650,547 and 4,890,620. All these approaches require the reduction of the molar glucose to oxygen ratio to extend the sensor range by relatively sophisticated means. Another approach is to put a semipermeable membrane between the enzyme layer and the whole blood sample such as those described in U.S. Pat. Nos. 4,757,022 and 4,759,828. Oxygen can diffuse across this semipermeable membrane much more easily than can glucose, typically at a ratio of more than 100 to 1. This membrane drastically slows down the diffusion rate of glucose and thus creates a more favorable glucose to oxygen molar ratio to prevent premature saturation of the sensor. The present invention eliminates the need for such a highly selective semipermeable membrane and thus allows the direct use of a fairly simple enzymatic glucose sensor in a dynamic mode with or without a semipermeable membrane.

3. Summary of the Invention

The present invention provides a method of using a simple glucose oxidase-based electrochemical sensor to measure the glucose concentration in biological fluids, especially body fluid, particularly human blood. In this present invention, the sensor is initially exposed to a glucose-free or low-glucose, oxygen-containing solution to register its oxygen reduction limiting current, also known as the zero-glucose or low-glucose baseline. Then, a sample is allowed to come in contact with the sensor for a certain amount of time, such as 30 seconds, to allow glucose to diffuse into the enzyme layer until saturation occurs. Then, the sensor is removed from the sample and again placed in the glucose-free, or low-glucose, oxygen-containing solution to allow glucose trapped in the enzyme layer to diffuse away. Once the diffusion process is completed, the sensor output will return to its original zero-glucose, or low-glucose, baseline. Since the amount of glucose trapped in the enzyme layer is a function of the glucose concentration in the sample, the time it takes to return to the full zero-glucose, or low-glucose, baseline output, or a fraction of it, from the time the sensor is returned to the glucose-free, or low-glucose, solution (defined as time-to-recover) has now been discovered to be a function of the original glucose concentration in the sample alone if other conditions, especially sample exposure time and temperature, are held constant. By choosing an enzyme layer of a suitable thickness, sufficient resolution in time-to-recover enables us to accurately measure samples ranging in glucose concentration from approximately 50 to 600 milligrams/deciliter with a single sensor.

In an attempt to further improve the resolution of the glucose sensor, a very thin membrane layer of a barrier material can be applied over the enzyme layer primarily to slow down the diffusion of glucose into and out of the sensor and in particular to slow down the diffusion of glucose to the immobilized enzyme layer of the sensor. This barrier membrane layer is typically less than 0.001 inches thick but may also be less than 0.010 inches thick and may be a polycarbonate film or a perfluorinated ionomer membrane such as that ionomer membrane sold under the trade name Nafion. This barrier membrane layer typically has a low diffusion coefficient for glucose and high diffusion coefficient for oxygen and must in general be more than 0.00001 inches thick. It not only slows down glucose diffusion out of the enzyme layer for better resolution but also permits oxygen in the baseline solution to reach the sensing electrode in time for the time-to-recover measurement. However, in its operation here it acts differently from the conventional glucose sensor approach described in 4,650,574 which requires the barrier to maintain a glucose to oxygen ratio of at least 1 to 100 to avoid sensor signal saturation over the range of clinical interest, 50–600 mg/dl. This present invention works even at a ratio 1 to 10 or below because it does not quantitatively determine glucose concentration based on the measurement oxygen current directly. Therefore, it is no longer critical to avoid sensor saturation due to lack of oxygen in the enzyme layer. In addition, unlike conventional enzymatic glucose sensors operating in the oxygen reduction mode, this present invention does not require a knowledge of $pO_2$ in the sample to compensate for an initial offset in the event that $pO_2$ values may be expected to vary over a wide range in the case of critically ill patients.

The specific form of the time-to-recover versus sample glucose concentration function depends on the structure of the sensor. In practice, an empirical calibration curve can be obtained to translate recovery time into glucose concentration.

DETAILED DESCRIPTION OF THE INVENTION

A novel sensing method has been developed to measure blood glucose intermittently. The method takes advantage of the fact that conventional enzyme-based (glucose oxidase) glucose sensors suffer from a low limiting range problem which renders them useless in clinical settings. A method has now been discovered that utilizes the exposure of a glucose sensor first in an oxygen-containing, but glucose-free, or nearly glucose-free, solution to establish its zero-glucose, or low-glucose, baseline output, followed by exposure to a sample in which glucose is to be determined for a certain period of time to allow saturation to take place. The sensor is then returned to the original zero-glucose, or low-glucose, solution to allow the glucose trapped in the enzyme layer to diffuse away and baseline output to return. It has now been discovered that the amount of time required for the baseline to recover can be reproducibly correlated to the glucose content in the sample.

The glucose sensor developed is essentially composed of a polarographic oxygen electrode assembly coated with an immobilized enzyme layer. On top of this glucose sensor there can also be a thin perfluorinated ionomer or polycarbonate barrier film.

This measurement process must be repeatable in a very reproducible manner to ensure a high level of accuracy. To this end, as an example, the invention can take advantage of the fluid handling capability of the blood chemistry system manufactured by VIA Medical Corporation which withdraws a precise amount of blood sample and then displaces the sample with an infusible intravenous (I.V.) fluid in a reproducible fashion, as is described in U.S. Pat. No. 4,573,968.

Specifically, the present invention can be embodied in a sensor assembly suitable for use in a combined intravenous (I.V.) fluid delivery and blood chemistry monitoring system. The sensor is located in the I.V. line near the patient end, as described in U.S. Pat. No. 4,573,968. Most of the time the glucose sensor is in the I.V. fluid which contains virtually no glucose at all and the sensor signal is thus the zero-glucose baseline. Its output is proportional to the $pO_2$ level in the I.V. solution which is essentially the partial pressure of oxygen in ambient air. The control system for the assembly, which is a microprocessor-based reversible peristaltic pump, controls the fluid movement in both directions. In a measurement cycle, blood is drawn up into the infusion line and made to flow past the glucose sensor. The blood sample then is in immediate contact with the glucose sensor for a fixed amount of time during which the sensor output drops to near zero, that is to the background current, due to the above referenced saturation reaction. The blood is then purged from the sensor assembly by the I.V. fluid. The sensor output then returns to its original baseline level over time. It has now been discovered that the time-to-recover of the sensor varies in a systematic and reproducible manner which depends upon the glucose concentration in the blood sample. By this method it has been discovered that glucose concentrations can be quantitatively determined by measuring the time it takes the sensor to recover from exposure to a blood sample.

The glucose sensing sequences involved are:

1. The polarization of the glucose sensor in an oxygen-containing, glucose-free or low-glucose solution until a steady current is obtained and the recording of this baseline current $I_o$. This baseline output may be measured as a current, or through appropriate electronic means as a voltage or as a mechanical dial position or other appropriate means.
2. The withdrawal of a blood sample from a patient at a fixed flow rate, $F_w$, and for a fixed period of time, $T_w$, allowing blood to stay in contact with the glucose sensor for time $T_e$, and the recording of the final current output $I_e$ at the end of time $T_e$.
3. The flushing of the blood sample with an oxygen-containing glucose-free (or low-glucose) I.V. solution at a fixed rate, $F_f$, for a fixed time, $T_f$.
4. The monitoring of the time required for the sensor output to recover to a certain percentage, x%, of the overall signal drop, as for example $I_o - I_e$, starting from the beginning of the flush and the recording of this time-to-recover is defined as $T_r$.
5. The determination of the glucose concentration of the sample from a calibration curve which is obtained with solutions of known glucose levels for the sensor.

The time-to-recover, $T_r$, for a particular sensor is dependent on the structure of the membrane layers, the oxygen partial pressure of the oxygen-containing solution and the oxygen and glucose levels in the blood. In other words, $T_r$ is a function, F, of $L_e$, $L_p$, $C_o^b$, $C_g^b$, $C_o^c$, and $C_g^c$, and thus:

$$T_r = F(L_e, L_p, C_o^b, C_g^b, C_o^c, \text{ and } C_g^c)$$

where $L_e$ = The thickness of the enzyme layer
$L_p$ = The thickness of the barrier layer
$C_o^b$ = The concentration of oxygen in the blood sample
$C_g^b$ = The concentration of glucose in the blood sample
$C_o^c$ = The concentration of oxygen in the oxygen-containing solution
$C_g^c$ = The concentration of glucose in the oxygen-containing solution Since $C_o^c$ and $C_g^c$ are known and $L_e$ and $L_p$ are fixed for a specific sensor, $$T_r = T_r(C_o^b, C_g^b)$$

The enzyme layer is almost always starved of oxygen after exposure to blood for some time because most clinical samples contain about 2 orders of magnitude more glucose than oxygen. The oxygen profiles in the enzyme layers then are almost identical before flushing of the blood sample. The only variation before flushing is the oxygen profile within the permselective membrane. Since the oxygen partial range in venous blood is narrow and low compare to the air-containing solution ($pO_2 = 150$ mm Hg), one can deduce that the contribution of $C_o^b$ is minor and that $T_r$ is almost exclusively a function of the glucose concentration in the sample.

PREFERRED EMBODIMENT

As a preferred embodiment of the present invention, the time-to-recover values of different blood samples were measured according to the method of this invention:

In this embodiment, a polarographic oxygen electrode assembly having a platinum (Pt) working electrode and a silver/silver chloride (Ag/AgCl) counter electrode was fabricated and placed in a flow cell. A gel mixture composed of glucose oxidase, human serum albumin, polyvinyl alcohol and glutaraldehyde was prepared and coated onto the oxygen electrode surfaces. Table 1 shows the concentrations of various ingredients in the gel mixture.

TABLE 1

Typical Composition of Glucose Oxidase Gel

| Ingredient | Approximate weight percent (wt %) |
|---|---|
| glucose oxidase | 8.5 |
| human serum albumin | 3.5 |
| polyvinyl alcohol | 0.5 |
| glutaraldehyde | 1.0 |
| distilled water | balance |

The enzyme gel layer was applied to the oxygen electrode by dispensing a drop of the mixture onto the working electrode surface, brushing the mixture onto the electrode, or dip coating the electrode surface in the mixture. The gel coating is allowed to dry at ambient temperature or below ambient temperature. The enzyme is thus immobilized in this layer through a cross-linking process involving glutaraldehyde. This process is followed by putting a drop of a dilute ethanol solution of perfluorinated ionomer, such as Nafion, or a dilute solution of polycarbonate in a volatile organic solvent over the enzyme layer to form a glucose diffusion barrier to slow down the diffusion of glucose to the gel-coated oxygen electrode assembly to form the glucose sensor.

The resulting glucose sensor is connected to a monitor which consists of a reversible peristaltic I.V. infusion pump, capable of handling fluids into and out of an I.V. cannula. The following settings, as defined earlier, are used:

$F_w = 200$ ml/hr
$T_w = 8.1$ sec
$F_f = 999$ ml/hr
$T_f = 16.2$ sec
$T_e = 30.0$ sec The baseline fluid is an air-saturated physiologic saline solution, such as lactated Ringer's solution. The glucose sensor is then tested with an aqueous solution containing a known level of glucose as well as with human blood samples. The glucose levels in the blood were first measured by a STAT PROFILE 5 analyzer manufactured by NOVA Biomedical, Waltham, Mass., which employs a glucose oxidase-based glucose sensor with a glucose diffusion limited membrane as described in U.S. Pat. No. 4,759,828.

In a typical cycle, the glucose sensor of this embodiment is exposed to the oxygen-containing I.V. infusion solution and the magnitude of the signal is proportional to the oxygen partial pressure in the solution. Upon introduction of a blood sample to the glucose sensor by reversing the I.V. pump to withdraw blood from the cannula, the signal begins to fall and eventually reaches a background level, indicating sensor saturation. The amount of time required to reach saturation is a function of the barrier property and the glucose concentration in the blood sample. Afterward, the blood is flushed away from the sensor by a forward pumping motion and the glucose sensor signal recovers to its original level some time later. As shown in Table 2, this time period, that is the time-to-recover, is a function of the glucose concentration in the blood. It has now been discovered that glucose concentration is proportional to the cube of time-to-recover in this particular sensor structure. In other words, a plot of the cube of time-to-recover, versus glucose concentration is a straight line and this straight line is the calibration plot for this sensor. In this case, as shown by the data listed in Table 2, the straight line has a slope of 5556 $sec^3$/mg/dl and a least-square fit coefficient of 0.996. In practice, one can determine the slope of this calibration plot by measuring the time-to-recover of the glucose sensor using one or more samples of known glucose levels. If only one sample is used, it automatically assumes a zero intercept, i.e. the time-to-recover is 0 with zero glucose. Two or more solutions may be preferred to ensure better accuracy.

TABLE 2

Recovery Time vs. Glucose Concentration

| Glucose Concentration (mg/dl) | Recovery Time, $T_r$ (sec) | $T_r^3$ ($sec^3$) |
|---|---|---|
| 50 | 50 | 125,000 |
| 120 | 85 | 614,125 |
| 240 | 110 | 1,331,000 |
| 400 | 130 | 2,197,000 |
| 600 | 150 | 3,375,000 |

This method has been employed to measure the glucose concentrations in two blood samples and the results are compared with those obtained from a NOVA STAT PROFILE 5, as shown in Table 3. In blood sample 1, the time-to-recover, $T_r$, was found to be 90 seconds, while in blood sample 2, the time-to-recover, $T_r$, was found to be 135 seconds. The cubes of these times are therefore 729,000 and 2,460,375 $sec^3$, respectively, and by comparison of these values with Table 2 and with interpolation the glucose contrations are found by this invention to be those shown in Table 3.

TABLE 3

| | Glucose concentration (mg/dl) | |
|---|---|---|
| Blood Sample | This Invention | Commercial Glucose Meter |
| 1 | 130 | 125 |
| 2 | 450 | 440 |

In another embodiment, the method of this invention can be applied to any electrode configuration, including two or three electrode electrochemical enzymatic glucose sensors, regardless of electrode geometry and materials, as long as the sensors operate in the oxygen mode.

The present invention is not limited to a patient-attached system. As long as there is a means to move the zero-glucose, or low-glucose, solution and sample to the sensor in a controlled and reproducible manner. Specifically, a glucose senor may be placed in a bench top analyzer where fluids are moved to the sensor by pumps in the sequence described. The zero-glucose, or low-glucose, solutions do not have to be physiological saline infusion solutions. Any solution with sufficient buffer capacity and ionic strength to support the measurement of oxygen reduction would serve the purpose in this case.

Other sensor membrane structures may be used. The present invention is not limited to using the two layer design described above. For instance, a relatively thick single immobilized glucose oxidase layer may be used. Other additives may be incorporated directly into the immobilized glucose oxidase layer to retard glucose diffusion to improve the resolution of the sensor.

I claim:

1. A method for measuring a glucose content of a body fluid using an electrochemical glucose sensor, said method consisting essentially of:

exposing said sensor, said sensor using oxygen partial pressure as an indirect measurement of glucose concentration, in an oxygen-containing, low-glucose solution until a baseline sensor output is obtained;

exposing said sensor, after said exposure, to an oxygen-containing, glucose-containing sample of body fluid for a time sufficient to reach glucose saturation of said sensor;

removing said sensor from said oxygen-containing, glucose-containing sample of body fluid followed by returning said sensor to said low-glucose solution;

measuring a time required for said sensor output to reach a fixed level compared to said baseline sensor output, said time being called measured time-to-recover; determining a calibration time-to-recover by exposing said glucose sensor to at least one solution containing oxygen and having a known glucose concentration until glucose saturation of the sensor output is reached, followed by removing said sensor from said solution of known glucose concentration followed by placing of said sensor in said oxygen-containing, low glucose solution and measuring a time required for said sensor output to reach a fixed level compared to said baseline sensor output, said time being called calibration time-to-recover; and measuring the glucose content of said sample of body fluid by comparing said measured time-to-recover to said calibration time-to-recover.

2. A method of measuring said glucose content of a body fluid as disclosed in claim 1 wherein said body fluid is blood.

3. A method of measuring said glucose content of a body fluid as disclosed in claim 1 wherein said oxygen-containing low-glucose solution contains essentially zero glucose.

4. A method of measuring the glucose content of a body fluid as described in claim 1 wherein said glucose sensor is essentially a polarographic oxygen electrode assembly coated with a surface layer containing an enzyme that catalyzes the reaction of glucose with oxygen.

5. A method of measuring the glucose content of a body fluid as described in claim 4 wherein said enzyme is glucose oxidase.

6. A method of measuring the glucose content of a body fluid as described in claim 4 wherein said surface layer is less than 0.01 inch thick but more than 0.00001 inch thick.

7. The method of measuring the glucose content of a body fluid as described in claim 4 wherein said polarographic oxygen electrode assembly coated with a surface layer of an enzyme that catalyzes the reaction of glucose with oxygen is additionally coated with a membrane that is more permeable to oxygen than to glucose.

8. The method of measuring the glucose content of a body fluid as described in claim 7 wherein said membrane consists essentially of a perfluorinated ionomer.

9. The method of measuring the glucose content of a body fluid as described in claim 4 wherein said polarographic oxygen electrode assembly consists essentially of a platinum working electrode and a silver/silver chloride counter electrode and wherein said surface layer comprises a gel mixture containing an enzyme to catalyze the oxidation of glucose.

10. A method of measuring the glucose content of a body fluid as described in claim 9 wherein said gel mixture of an enzyme that catalyzes the oxidation of glucose consists essentially of glucose oxidase, human serum albumin, polyvinyl alcohol and glutaraldehyde.

11. A method for measuring the glucose level in body fluid, said method consisting essentially of;

exposing a glucose sensor to a low-glucose, oxygen-containing baseline solution by moving said baseline solution between a solution container and said glucose sensor using a fluid flow device;

measuring an output of said glucose sensor while said sensor is exposed to said low-glucose, oxygen-containing baseline solution; purging said low-glucose, oxygen-containing baseline solution;

exposing said glucose sensor to a sample of body fluid which contains oxygen and glucose by moving said sample of body fluid using a fluid flow device, for a time sufficient to reach glucose saturation of the output of said sensor; purging said sample of body fluid which contains oxygen and glucose from the said glucose sensor and returning said baseline solution to said sensor;

measuring the time required for said sensor output to reach a fixed level as compared to the original baseline output, said time being called measured time-to-recover;

determining a calibration time-to-recover by exposing said glucose sensor to at least one calibration solution containing oxygen and having a known glucose concentration, by moving said calibration solution using a fluid flow device, for a time sufficient to reach glucose saturation of the output of said sensor, purging of said calibration solution from said glucose sensor and returning said baseline solution to said sensor, and measuring the time required for said sensor output to reach a fixed level as compared to the original baseline output, said time being called calibration time-to-recover; and measuring the glucose content of said sample of body fluid by comparing said measured time-to-recover of said sensor to said calibration time-to-recover.

12. A method of measuring the glucose content of a body fluid as described in claim 11 wherein said body fluid is blood.

13. A method of measuring the glucose content of a body fluid as described in claim 11 wherein said low-glucose solution contains essentially zero glucose.

14. A method of measuring the glucose content of a body fluid as described in claim 11 wherein said glucose sensor is essentially a polarographic oxygen electrode assembly coated with a surface layer containing an enzyme that catalyzes the reaction of glucose with oxygen.

15. A method of measuring the glucose content of a body fluid as described in claim 14 wherein said enzyme is glucose oxidase.

16. A method of measuring the glucose content of a body fluid as described in claim 14 wherein the polarographic oxygen electrode assembly coated with a surface layer of an enzyme that catalyzes the reaction of glucose with oxygen is additionally coated with a membrane that is more permeable to glucose than to oxygen.

17. A method of measuring the glucose content of a body fluid as described in claim 16 wherein said membrane consists essentially of a perfluorinated ionomer.

18. A method of measuring the glucose content of a body fluid as described in claim 17 wherein said layer of membrane material is less than 0.010 inch thick but more than 0.00001 inch thick.

19. A method of measuring the glucose content of a body fluid as described in claim 11 wherein said glucose sensor is coated with a surface layer which is a gel mixture of an enzyme that catalyzes the oxidation of glucose.

20. A method of measuring the glucose content of a body fluid as described in claim 19 wherein said gel mixture of an enzyme that catalyzes the oxidation of glucose consists essentially of glucose oxidase, human serum albumin, polyvinyl alcohol and glutaraldehyde.

21. An improved method for measuring glucose content of a body fluid using an electrochemical glucose sensor, wherein said improvement consists essentially of:

exposing said sensor, said sensor using oxygen partial pressure as an indirect measurement of glucose concentration, in an oxygen-containing, low-glucose solution until a baseline sensor output is obtained;

exposing said sensor to an oxygen-containing, glucose-containing sample of body fluid for a time sufficient to reach glucose saturation of said sensor;

removing said sensor from said oxygen-containing, glucose containing sample of body fluid followed by returning said sensor to said low-glucose solution;

measuring a time required for said sensor output to recover to a fixed level compared to said baseline sensor output, said time being called measured time-to-recover;

determining a calibration time-to-recover by exposing said glucose sensor to at least one solution containing oxygen and having a known glucose concentration until glucose saturation of the sensor output is reached, followed by removing said sensor from said solution of known glucose concentration followed by placement of said sensor in said oxygen-containing, low glucose solution and measuring a time required for said sensor output to recover to a fixed level compared to said baseline output, said time being called calibration time-to-recover; and measuring the glucose content of said sample of body fluid by comparing said measured time-to-recover with said calibration time-to-recover.

* * * * *